US00PP12253P2

(12) United States Plant Patent
Drewlow

(10) Patent No.: US PP12,253 P2
(45) Date of Patent: Dec. 4, 2001

(54) STREPTOCARPUS PLANT NAMED 'MERCURY'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/573,118

(22) Filed: May 17, 2000

(51) Int. Cl.[7] ..... A01H 5/00

(52) U.S. Cl. ..... Plt./333

(58) Field of Search ..... Plt./333

*Primary Examiner*—Bruce R. Campell
*Assistant Examiner*—Kent L. Bell
(74) *Attorney, Agent, or Firm*—Webb Ziensenheim Logsdon Orkin & Hanson, P.C.

(57) ABSTRACT

A Streptocarpus plant named Mercury characterized by the combined characteristics of relatively large and violet colored flowers with white netting which are long-lasting, non-shattering, and continuously bloom under low light conditions of winter and high temperatures of summer.

2 Drawing Sheets

The present invention relates to a new and distinct cultivar of Streptocarpus plant, botanically known as *Streptocarpus*× *hybridus*, and known by the cultivar name Mercury. 'Mercury' was developed through controlled breeding by crossing Mikkelsen Seedling No. 92-167-6 (seed parent) (unpatented) with Mikkelsen Seedling No. 92-150-2 (pollen parent) (unpatented). The seed and pollen parents are proprietary breeding lines which have not been sold or made publicly available in this country.

Asexual reproduction of leaf cuttings has shown that the unique features of this new Streptocarpus are stabilized and are reproduced true to type in successive propagations. The plant was propagated in Ashtabula, Ohio.

The following characteristics distinguish the new Streptocarpus from other cultivated Streptocarpus of this type known to the inventor. The characteristics are described with comparative reference to the cultivars Demeter (unpatented) and Sirius (unpatented).

1. 'Mercury' has flowers colored Violet Group 87A netted with White Group 155C while 'Demeter' has a more purple-violet color of Violet Group 88B with heavier White Group 155C netting. 'Sirius' has deep purple color of Violet Group 86A with netting of Violet Group 86D.

2. 'Mercury' has a 50 to 55 mm flower diameter which is similar to 'Demeter' and larger than 'Sirius' (45 to 50 mm).

3. 'Mercury' has a white eye which is intermediate in diameter between 'Demeter' which has a very large eye and 'Sirius' which has no eye.

4. 'Mercury' has a red-purple cast to the midrib of the leaf and veins on young leaves while 'Demeter' and 'Sirius' each have midribs and veins on underside of leaves.

5. 'Mercury' has more serration on the edge of petals than either of 'Demeter' and 'Sirius'.

6. 'Mercury' has a red-purple cast to the ovary which similar to 'Demeter' while 'Sirius' has a green ovary.

7. 'Mercury' has leaves 15 to 18 cm long and 5 to 6 cm wide with 'Demeter' having leaves 15 to 18 cm long and 4.5 and 5 cm wide and 'Sirius' having shorter leaves at 12 to 15 cm long and 5 to 6 cm wide.

The accompanying colored photographs illustrate the overall appearance of the cultivar taken as a face view of the plant and showing the colors as true as it is reasonably possible to obtain in colored reproductions of this type.

Figure 1:
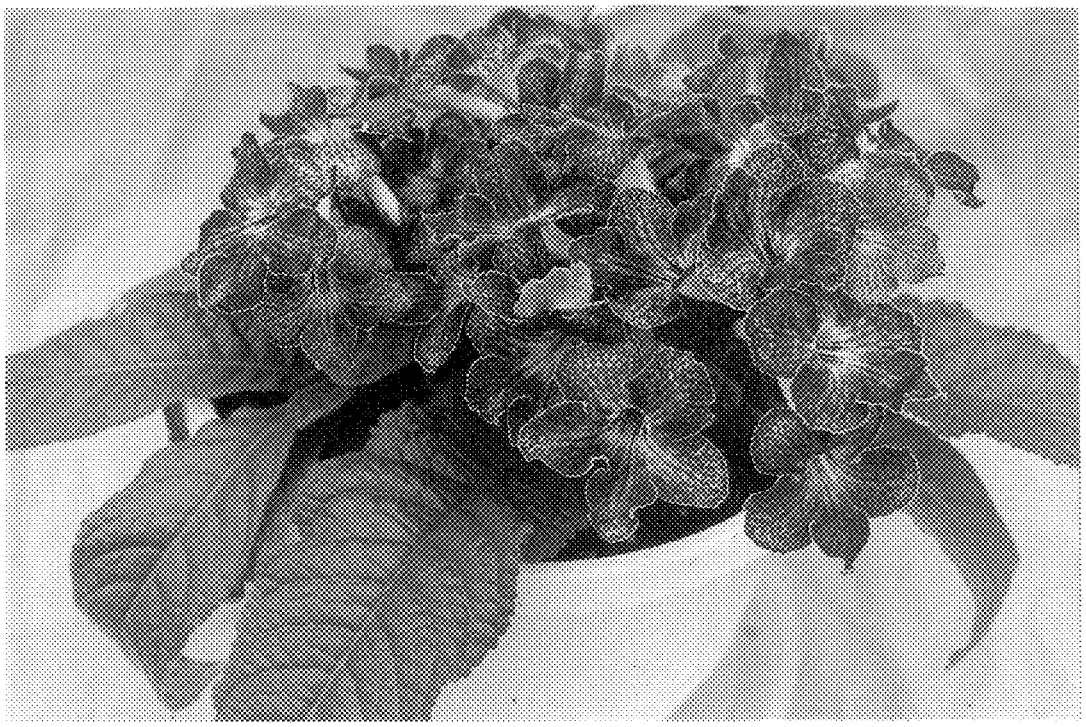
FIG. 1 is an overall view of the plant.
Figure 2:
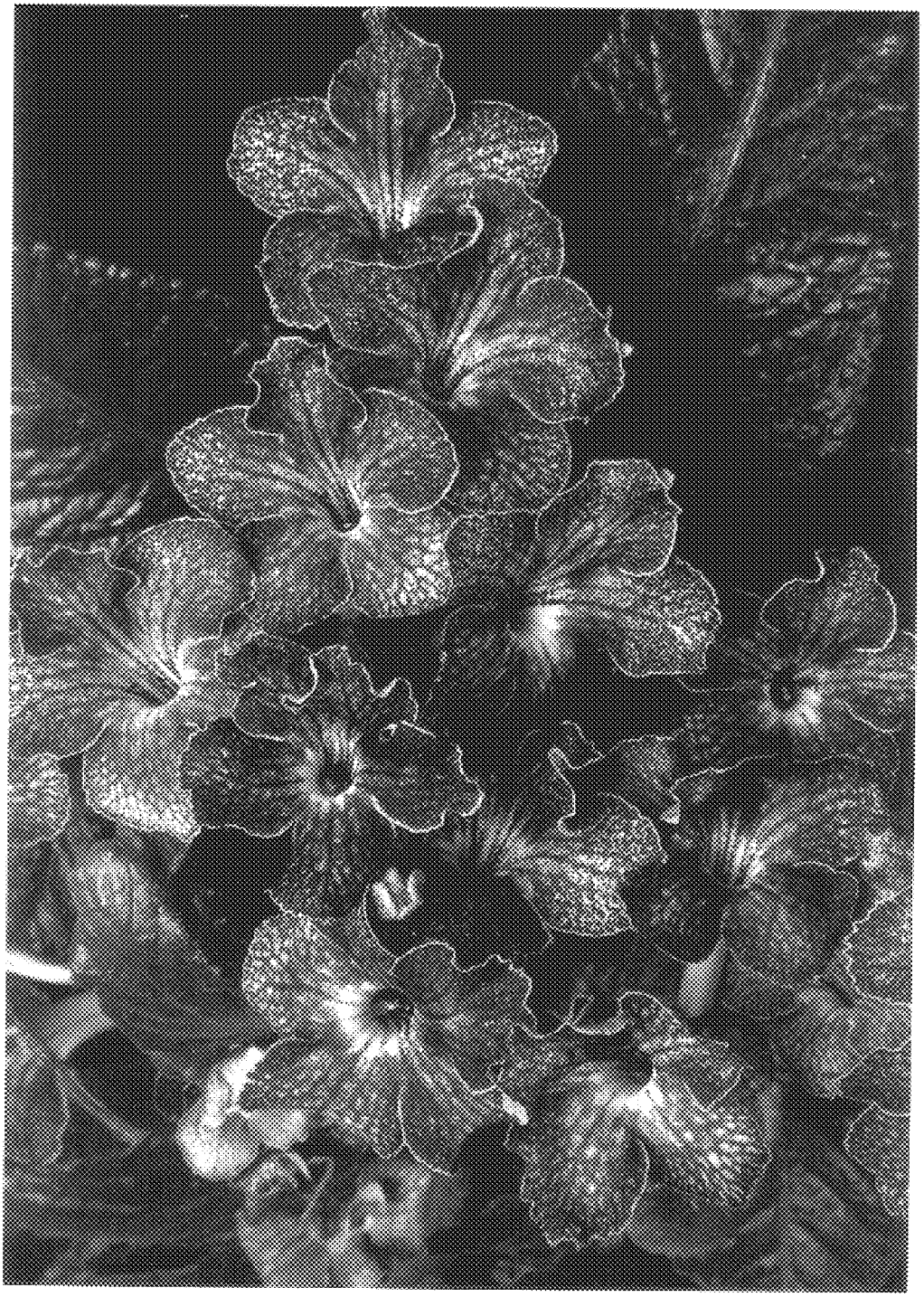
FIG. 2 is a close-up view of the flowers.

The following is a detailed description of my new cultivar, based on plants produced in greenhouses in Lompoc, Calif. during the winter season of the year. Plants were grown in 10 cm pots and measurements were taken 12 weeks after rooted cuttings were planted. Height measurements were taken from the soil line of the container. The plants were grown at 16° C. night temperatures 2500–3500 foot candles of light and 200 ppm nitrogen, 75 ppm potassium and 200 ppm phosphorous nutritional levels, with trace elements added. Habit of growth, foliage coloration, size of leaves and flower size will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 92-167-6 and male parent Mikkelsen Seedling No. 92150-2.

Propagation:

(*A*) *Type cutting.*—Leaf.

(*B*) *Time to develop.*—8 weeks at 22° C. summer; 8 weeks at 22° C. winter.

(*C*) *Root Description.*—Fine, abundant, fibrous.

Plant description:

*Habit and form of growth.*—Vigorous, leaves are in a rosette extending from a crown at soil line. Leaves form around plant to produce a symmetrical plant with flower stalks forming at basal area of midrib of each mature leaf; flowers are carried above foliage. Fruit/seed not produced.

*Height.*—13 to 15 cm from soil line at maturity.

*Foliage description.*—Spread: 25 to 30 at maturity. (1) Size: 15 to 18 cm in length and 5 to 6 cm wide at maturity. (2) Quantity: More than 15 leaves on a mature plant. (3) Shape: Elliptical to oblanceolate. (4) Texture: Lower surface rugose with veins protruding and pubescent; upper surface rugose and pubescent. (5) Margin: Finely crenate. (6) Color: Young foliage top side is Yellow-Green Group 146A, underside is Yellow-Green Group 148C. Mature foliage top side is Yellow-Green Group 147A, underside is Yellow-Green Group 148B. (7) Ribs and veins: Pinnate. (8) Rib and vein color: Yellow-Green Group 146C with Red-Purple Group 184B only on the bottom of the midrib and on young leaves and veins. (9) Leaf tips: Obtuse. (10) Leaf Base: Acute. (11) Leaves are stalked and have petioles. The petioles are 25 mm long, 10 mm in diameter, and have a Red-Purple Group 184A color.

Flower:

*Flower opening.*—Open one at a time on individual flower stalks.

*Fully expanded.*—50 to 55 mm in diameter.

*Stem.*—Single, Yellow-Green Group 146B with Red-Purple Group 184D cast, round, length is typically 12 cm and diameter is typically 3 mm, pubescent, several from a leaf midrib.

*Form.*—Funnel-shaped, corolla cylindrical 5 lobed, lobes orbicular to obovate with 2 upper petals slightly smaller than the 3 bottom petals. Open flower has ruffled appearance. Calyx deeply five-parted with no tube.

*Flower bud.*—Immature bud hangs downward, raising as matures. At maturity is 23 to 25 mm long with 5 green with sepals in calyx folded over basal end. The bud diameter is 5 mm and the bud shape is linear to oblong and tubular. The sepals have a length of 7 mm, a width of 2 mm, an entire margin, an acute apex, a truncate base, and a Yellow-Green Group 146B color with a Red-Purple Group 184D cast.

*Flowers borne.*—In clusters of usually 2 flowers per flower stalk on a mature plant carried above the foliage. Pedicels of both flowers on stalk are 10 to 11 mm long, and have a Yellow-Green Group 146B color with a Red-Purple Group 184D cast.

*Quantity of flowers.*—Mature plant can have 10 to 15 flower stalks with usually 2 flowers open per stalk.

*Permanence.*—Approximate time period for bloom lastingness is 10 to 12 days.

Color:

*Tonality from a distance.*—Violet netted pattern on a base of white with two upper petals having a white eye area and all five petals having a white margin at the edge of each petal.

*Front of petals.*—Violet Group 87A with White Group 155C base to netting and petal margin.

*Reverse of petals.*—Violet Group 84D with netting of Violet Group 87B.

*Throat.*—White Group 155C with Violet Group 87A streaking especially in the lower 3 petals.

*Discoloration.*—Areas in white part of netting increase.

Petals:

*Texture.*—Satin.

*Appearance.*—Individual lobed with crenate margins on upper part of each petal, top 2 petals are reflexed and smaller than bottom petals which are flat and slightly contorted. Length is 30 mm fused and 20 mm not fused. Width is 25 mm. The margin is crenate and the apex is obtuse to rounded.

*Arrangement.*—Circular in shape with deep cuts between the petals.

*Persistence.*—Will dry on the plant before finally dropping off.

*Fragrance.*—None.

Reproductive organs:

*Stamens.*—2 fertile interconnected by the anthers, 2 sterile and very small. (1) Anther: 2 fertile interconnected and flat in shape, white with violet cast in color. (2) Filament: 2 fertile are free standing for 5 mm and sterile for 1 mm, the balance of the filament is fused to the petals, white with violet cast in color. (3) Pollen: Abundant, white color.

*Pistils-Number.*—2 — (1) Stigma shape: Flattened with reflexed tips. Color: White with violet cast. Size: 2 mm in diameter. (2) Style: Color: White with violet cast. Size: 7 mm in diameter. (3) Ovaries: Number: 1 with over 500 ovules. Size: 12 to 14 mm in diameter on a receptive pistil. Color: green with violet cast.

Disease resistance: No disease problems seen to date.

OTHER IMPORTANT CHARACTERISTICS

1. 'Mercury' has numerous short leaves in a rosette instead of a few large leaves that characterize many older Streptocarpus cultivars. This results in a very floriferous plant with flowers clustered in middle of green foliage making an attractive 15 cm plant.

2. Flowers are long-lasting, non-shattering and leaves are small and pliable making this cultivar easy to ship.

3. 'Mercury' has shown the ability to flower year round during higher temperatures of summer and lower light levels of winter under greenhouse conditions.

4. 'Mercury' does not foliar spot when watered with 10° C. water and tolerates fairly high light levels (2500 foot candles) without the leaves bronzing.

I claim:

1. A new and distinct cultivar of Streptocarpus plant named 'Mercury', as illustrated and described.

* * * * *

UNITED STATES PATENT AND TRADEMARK OFFICE

CERTIFICATE OF CORRECTION

PATENT NO. : PP 12,253 P2
DATED : December 4, 2001
INVENTOR(S) : Lyndon W. Drewlow It is certified that error appears in the above-identified patent and that said Letters Patent is hereby corrected as shown below:

Column 1,
Lines 33-34, "which similar" should read -- which is similar --.
Lines 36-37, "4.5 and 5 cm" should read -- 4.5 to 5 cm --.

Column 2,
Line 19, "92150-2" should read -- 92-150-2 --.
Line 33, "25 to 30 at" should read -- 25 to 30 cm at --.

Signed and Sealed this

Twentieth Day of August, 2002

*Attest:*

*Attesting Officer*

JAMES E. ROGAN
*Director of the United States Patent and Trademark Office*